(12) United States Patent
Gavriely et al.

(10) Patent No.: US 8,771,205 B2
(45) Date of Patent: *Jul. 8, 2014

(54) COUGH DETECTOR

(75) Inventors: Oren Gavriely, Haifa (IL); Noam Gavriely, Haifa (IL)

(73) Assignee: Isonea Limited, Armadale, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/571,876

(22) Filed: Aug. 10, 2012

(65) Prior Publication Data

US 2012/0302921 A1  Nov. 29, 2012

Related U.S. Application Data

(63) Continuation of application No. 11/912,897, filed as application No. PCT/IL2006/000517 on Apr. 30, 2006, now Pat. No. 8,241,223.

(60) Provisional application No. 60/675,829, filed on Apr. 29, 2005.

(51) Int. Cl.
*A61B 7/00* (2006.01)

(52) U.S. Cl.
USPC .......................... 600/586; 600/532; 600/538

(58) Field of Classification Search
USPC .......................... 600/532, 586; 327/40, 44, 47
See application file for complete search history.

(56) References Cited

U.S. PATENT DOCUMENTS

| | | | |
|---|---|---|---|
| 3,990,435 A | 11/1976 | Murphy | |
| 4,009,616 A | 3/1977 | Wonn | |
| 4,094,304 A | 6/1978 | Wright | |
| 4,115,356 A | 9/1978 | Hillard | |
| 4,140,281 A | 2/1979 | Fulghum et al. | |
| 4,155,356 A | 5/1979 | Venegas | |
| 4,173,897 A | 11/1979 | Forstermann et al. | |
| 4,197,856 A | 4/1980 | Northrop | |
| 4,240,281 A | 12/1980 | Lather et al. | |
| 4,306,567 A | 12/1981 | Krasner | |
| 4,326,416 A | 4/1982 | Fredberg | |

(Continued)

FOREIGN PATENT DOCUMENTS

| CA | 2262236 C | 8/1999 |
|---|---|---|
| EP | 0371424 A1 | 11/1989 |

(Continued)

OTHER PUBLICATIONS

T. Rosqvist, et al. "Tool Kit for Lung Sound Analysis" Medical and Biological Engineering & Computing, vol. 33, No. 2 Mar. 1995, pp. 190-195.

(Continued)

*Primary Examiner* — Long V. Le
*Assistant Examiner* — Farshad Negarestan
(74) *Attorney, Agent, or Firm* — Shartsis Friese, LLP; Cecily Anne O'Regan

(57) ABSTRACT

A device for detecting and counting coughing events is provided. In one embodiment a sensor for sensing and transducing low frequency and high frequency mechanical vibrations, sends signals to a coincidence detector that determines if high and low signals coincide. In another embodiment, ultrasonic energy is introduced to the trachea and if Doppler shift in frequency is detected, association is made to a coughing event. In another embodiment a change in the impedance of the neck is considered associated with coughing event if correlated over time with a specific mechanical frequency sensed.

11 Claims, 6 Drawing Sheets

(56) References Cited

U.S. PATENT DOCUMENTS

| | | |
|---|---|---|
| 4,424,815 A | 1/1984 | Kuntz |
| 4,653,327 A | 3/1987 | Varterasian et al. |
| 4,671,295 A | 6/1987 | Abrams et al. |
| 4,672,977 A | 6/1987 | Kroll |
| 4,705,048 A | 11/1987 | Pfohl |
| 4,706,229 A | 11/1987 | Congdon |
| 4,830,015 A | 5/1989 | Okazaki |
| 4,951,678 A | 8/1990 | Joseph et al. |
| 4,982,738 A | 1/1991 | Griebel |
| 5,010,889 A | 4/1991 | Bredesen et al. |
| 5,058,600 A | 10/1991 | Schechter et al. |
| 5,134,995 A | 8/1992 | Gruenke et al. |
| 5,143,078 A | 9/1992 | Mather et al. |
| 5,165,417 A | 11/1992 | Murphy, Jr. |
| 5,213,108 A | 5/1993 | Bredesen et al. |
| 5,218,969 A | 6/1993 | Bredesen et al. |
| 5,239,997 A | 8/1993 | Guarino et al. |
| 5,259,373 A | 11/1993 | Gruenke et al. |
| 5,309,922 A | 5/1994 | Schechter et al. |
| 5,311,875 A | 5/1994 | Stasz |
| 5,316,002 A | 5/1994 | Jackson et al. |
| 5,318,038 A | 6/1994 | Jackson et al. |
| 5,331,967 A | 7/1994 | Akerson |
| 5,361,767 A | 11/1994 | Yukov |
| 5,417,215 A | 5/1995 | Evans et al. |
| 5,485,841 A | 1/1996 | Watkin et al. |
| 5,492,129 A | 2/1996 | Greenberger |
| 5,549,106 A | 8/1996 | Gruenke et al. |
| 5,553,609 A | 9/1996 | Chen et al. |
| 5,560,351 A | 10/1996 | Gravenstein et al. |
| 5,562,608 A | 10/1996 | Sekins et al. |
| 5,588,439 A | 12/1996 | Hollub |
| 5,591,130 A | 1/1997 | Denton |
| 5,620,004 A | 4/1997 | Johansen |
| 5,666,960 A | 9/1997 | Fredberg et al. |
| 5,671,733 A | 9/1997 | Raviv et al. |
| 5,746,699 A | 5/1998 | Fredberg et al. |
| 5,769,084 A | 6/1998 | Katz et al. |
| 5,782,240 A | 7/1998 | Raviv et al. |
| 5,797,852 A | 8/1998 | Karakasoglu et al. |
| 5,836,891 A | 11/1998 | DiMarogonas |
| 5,844,997 A | 12/1998 | Murphy, Jr. |
| 5,882,314 A | 3/1999 | Fredberg et al. |
| 5,884,997 A | 3/1999 | Stanuch et al. |
| 5,893,361 A | 4/1999 | Hughes |
| 5,919,139 A | 7/1999 | Lin |
| 5,919,144 A | 7/1999 | Bridger et al. |
| 6,045,514 A | 4/2000 | Raviv et al. |
| 6,058,932 A | 5/2000 | Hughes |
| 6,062,216 A | 5/2000 | Corn |
| 6,116,241 A | 9/2000 | Huygen et al. |
| 6,139,505 A | 10/2000 | Murphy |
| 6,142,952 A | 11/2000 | Behbehani et al. |
| 6,164,277 A | 12/2000 | Merideth |
| 6,168,568 B1 | 1/2001 | Gavriely |
| 6,202,646 B1 | 3/2001 | Camodeca et al. |
| 6,213,955 B1 | 4/2001 | Karakasoglu et al. |
| 6,241,683 B1 | 6/2001 | Macklem et al. |
| 6,261,238 B1 | 7/2001 | Gavriely |
| 6,279,677 B1 | 8/2001 | Sanchez-Zambrano |
| 6,287,264 B1 | 9/2001 | Hoffman |
| 6,364,849 B1 | 4/2002 | Wilcox |
| 6,375,623 B1 | 4/2002 | Gavriely |
| 6,381,559 B1 | 4/2002 | Huang |
| 6,383,142 B1 | 5/2002 | Gavriely |
| 6,394,967 B1 | 5/2002 | Murphy |
| 6,428,483 B1 | 8/2002 | Carlebach |
| 6,432,057 B1 | 8/2002 | Mazess et al. |
| 6,440,083 B1 | 8/2002 | Fredberg et al. |
| 6,443,907 B1 | 9/2002 | Mansy et al. |
| 6,454,724 B1 | 9/2002 | Greene |
| 6,491,641 B1 | 12/2002 | Rasmussen |
| 6,517,497 B2 | 2/2003 | Rymut et al. |
| 6,580,944 B1 | 6/2003 | Katz et al. |
| 6,595,928 B2 | 7/2003 | Mansy et al. |
| 6,738,734 B1 | 5/2004 | Huang |
| 6,790,183 B2 | 9/2004 | Murphy |
| 6,811,538 B2 | 11/2004 | Westbrook et al. |
| 6,942,626 B2 | 9/2005 | Salisbury et al. |
| 7,127,290 B2 | 10/2006 | Girouard et al. |
| 7,347,824 B2 | 3/2008 | Wilkinson et al. |
| 7,479,115 B2 | 1/2009 | Savic |
| 7,520,861 B2 | 4/2009 | Murphy |
| 7,559,903 B2 | 7/2009 | Moussavi et al. |
| 7,708,697 B2 | 5/2010 | Wilkinson et al. |
| 7,819,814 B2 | 10/2010 | Gavriely et al. |
| 7,850,618 B2 | 12/2010 | Wilkinson |
| 8,241,223 B2 | 8/2012 | Gavriely et al. |
| 8,517,016 B2 | 8/2013 | Caro et al. |
| 2002/0002327 A1 | 1/2002 | Grant et al. |
| 2002/0014235 A1 | 2/2002 | Rogers et al. |
| 2002/0072685 A1 | 6/2002 | Rymut et al. |
| 2002/0183642 A1 | 12/2002 | Murphy |
| 2002/0193697 A1 | 12/2002 | Cho et al. |
| 2003/0033094 A1 | 2/2003 | Huang |
| 2003/0034035 A1 | 2/2003 | Raphael |
| 2003/0045806 A1 | 3/2003 | Brydon |
| 2003/0069502 A1 | 4/2003 | Makin et al. |
| 2003/0120182 A1 | 6/2003 | Wilkinson et al. |
| 2004/0010202 A1 | 1/2004 | Nakatani et al. |
| 2004/0059240 A1 | 3/2004 | Cho et al. |
| 2004/0069304 A1 | 4/2004 | Jam |
| 2004/0236241 A1 | 11/2004 | Murphy |
| 2004/0254493 A1 | 12/2004 | Chervin et al. |
| 2005/0005935 A1 | 1/2005 | Gradon |
| 2005/0011279 A1 | 1/2005 | Takeda et al. |
| 2005/0020932 A1 | 1/2005 | Haberland et al. |
| 2005/0027207 A1 | 2/2005 | Westbrook et al. |
| 2005/0043645 A1 | 2/2005 | Ono et al. |
| 2005/0096557 A1 | 5/2005 | Vosburgh et al. |
| 2005/0154307 A1 | 7/2005 | Hirayama et al. |
| 2005/0187464 A1 | 8/2005 | Ho et al. |
| 2006/0037615 A1 | 2/2006 | Wilkinson et al. |
| 2006/0243280 A1 | 11/2006 | Caro |
| 2007/0055175 A1 | 3/2007 | Caro |
| 2007/0118054 A1 | 5/2007 | Pinhas et al. |
| 2007/0161918 A1 | 7/2007 | Ganshorn |
| 2008/0146892 A1 | 6/2008 | LeBoeuf et al. |
| 2008/0177195 A1 | 7/2008 | Armitstead |
| 2008/0283062 A1 | 11/2008 | Esposito |
| 2009/0151718 A1 | 6/2009 | Hunter et al. |
| 2009/0171231 A1 | 7/2009 | Caro et al. |
| 2009/0203972 A1 | 8/2009 | Heneghan et al. |
| 2009/0216127 A1 | 8/2009 | Gavriely |
| 2010/0274554 A1 | 10/2010 | Orr et al. |
| 2011/0230777 A1 | 9/2011 | Fu |
| 2012/0215126 A1 | 8/2012 | Gavriely |
| 2012/0302921 A1 | 11/2012 | Gavriely |

FOREIGN PATENT DOCUMENTS

| | | |
|---|---|---|
| FR | 2299633 | 8/1976 |
| FR | 2672793 | 8/1992 |
| GB | 2055046 A | 2/1981 |
| GB | 2240392 A | 7/1991 |
| JP | 2005-066044 | 3/2005 |
| RU | 2177759 C1 | 1/2001 |
| WO | WO88/02237 A1 | 4/1988 |
| WO | WO91/03981 A1 | 4/1991 |
| WO | WO96/19142 A1 | 6/1996 |
| WO | WO97/00643 | 1/1997 |
| WO | WO97/29687 A1 | 8/1997 |
| WO | WO98/14116 A2 | 4/1998 |
| WO | WO98/14116 A3 | 4/1998 |
| WO | WO99/32035 A1 | 7/1999 |
| WO | WO99/52437 A1 | 10/1999 |
| WO | WO00/27282 A1 | 5/2000 |
| WO | WO00/22735 A1 | 6/2000 |
| WO | WO00/33735 A1 | 6/2000 |
| WO | WO00/44281 | 8/2000 |
| WO | WO01/80741 | 11/2001 |
| WO | WO01/80742 A1 | 11/2001 |
| WO | WO02/13677 A2 | 2/2002 |
| WO | WO02/13677 A3 | 2/2002 |

(56) References Cited

FOREIGN PATENT DOCUMENTS

| | | |
|---|---|---|
| WO | WO02/13697 A1 | 2/2002 |
| WO | WO02/30280 | 4/2002 |
| WO | WO02/41777 A1 | 5/2002 |
| WO | WO02/43579 A2 | 6/2002 |
| WO | WO02/43579 A3 | 6/2002 |
| WO | WO02/065901 A2 | 8/2002 |
| WO | WO02/065901 A3 | 8/2002 |
| WO | WO03/024335 | 3/2003 |
| WO | WO03/061471 | 7/2003 |
| WO | WO03/063701 A1 | 8/2003 |
| WO | WO03/071952 | 9/2003 |
| WO | WO03/075739 A2 | 9/2003 |
| WO | WO03/092493 A2 | 11/2003 |
| WO | WO03/092493 A3 | 11/2003 |
| WO | WO2004/091503 A2 | 10/2004 |
| WO | WO2004/091503 A3 | 10/2004 |
| WO | WO2010/086851 A1 | 8/2010 |
| WO | WO 2013/021383 | 2/2013 |
| WO | WO2013/021383 A1 | 2/2013 |
| WO | WO2013/043847 A1 | 3/2013 |

OTHER PUBLICATIONS

A. Cohen, et al.: "Analysis and Automatic Classification of Breath Sounds" IEEE Transactions on Biolmedical Engineering, vol. 31, No. 9, Sep. 1984, NY, USA pp. 585-590.

A. Cohen: "Signal Processing Methods for Upper Airway and Pulmonary Dysfunction Diagnosis", IEEE Engineering in Medicine & biology, vol. 9, No. 1, Mar. 1990, NY USA, pp. 72-75.

Wodicka et al.; "Bilateral Asymmetry of Respiratory Acoustic Transmission;" Sep. 1994; Medical & Biological Engineering & Computing; vol. 32, pp. 489-494; XP000469338.

Dalmay, et al. "Acoustic Properties of the Normal Chest" European Respiratory Journal (1995) vol. 8, pp. 1761-1769.

Pseudo-noise (PN). (2001). In Hargrave's Communications Dictionary, Wiley. Retrieved Dec. 5, 2007, from http://www.credoreference.com/entry/2723988.

"Pseudorandom noise" from Wikipedia, the free encyclopedia. Retrieved Dec. 5, 2007 from http://en.wikipedia.org/wiki/Pseudo-random.sub.--noise.

Murphy, R., et al. "Sound Speed in the Lung Measured by Sound Injection into Supraclavicular Space." European Respiratory Society Congress (2002) abstract.

Paciej, R., et al. "Transpulmonary Speed of Sound Input into Supraclavicular Space." J. Appl. Physiol (1994) vol. 94, pp. 604-611.

Bergstresser, T., et al. "Sound Transmission in the Lung as a Function of Lung Volume." J. Appl. Physiol. (2002) vol. 93, pp. 667-674.

Pasterkamp et al. "Respiratory Sounds—Advances Beyond the Stethoscope" American Journal of Respiratory and Critical Care Medicine (1997) vol. 156, pp. 975-985.

Karnath et al. "Pulmonary Auscultation" Hospital Physician (2002) pp. 22-26.

Leung et al. "Sound Transmission Between 50 and 600 Hz in Excised Pig Lungs Filled with Air and Helium" Journal of Applied Physiology (2000) vol. 89, Issue 6, pp. 2472-2482.

Wodicka et al. "Spectral Characteristics of Sound Transmission in the Human Respiratory System" IEEE Transactions on Biomedical Engineering (1990) vol. 37, No. 12, pp. 1130-1135.

Leung et al. "Sound Transmission Through Normal and Diseased Human Lungs" Engineering Science and Education Journal (1996) pp. 25-31.

Wodicka et al. "Phase Delay of Pulmonary Acoustic Transmission from Trachea to Chest Wall" IEEE Transactions on Biomedical Engineering (1992) vol. 39, No. 10, pp. 1053-1059.

Mahagnah et al. "Gas Density Does Not Affect Pulmonary Acoustic Transmission in Normal Men" Journal of Applied Physiology (1995) vol. 78, Issue 3, pp. 928-937.

Pohlmann et al. "Effect of Changes in Lung Volume on Acoustic Transmission through the Human Respiratory System" Physiological Measurement (2001) vol. 22, pp. 233-243.

Huang et al. "A New Nasal Acoustic Reflection Technique to Estimate Pharyngeal Cross-Sectional Area During Sleep" Journal of Applied Physiology (2000) vol. 88, pp. 1457-1466.

Poort et al. "Airway Area by Acoustic Reflection: A Corrected Derivation for the Two-Microphone Method" Journal of Biomechanical Engineering (1999) vol. 121, pp. 663-665.

Marshall et al. "Acoustic Reflectometry for Airway Measurements in Man: Implementation and Validation" Physiological Measurement (1993) vol. 14, pp. 157-169.

Louis et al. "Airway Area by Acoustic Reflection: The Two-Microphone Method" Journal of Biomechanical Engineering (1993) vol. 115, pp. 278-285.

Rubinstein et al. "Effect of Mouthpiece, Noseclips, and Head Position on Airway Area Measured by Acoustic Reflections" The American Physiological Society (1987) pp. 1469-1474.

Brooks et al. "Reproducibility and Accuracy of Airway Area by Acoustic Reflection" Journal of Applied Physiology (1986) vol. 57, pp. 777-787.

Fredberg et al. "Airway Area by Acoustic Reflections Measured at the Mouth" Journal of Applied Physiology (1980) vol. 48, pp. 749-758.

Sidell et al. "Noninvasive Inference of Airway Network Geometry from Broadband Lung Reflection Data" Journal of Biomechanical Engineering (1978) vol. 100, pp. 131-138.

Jackson et al. "Airway Geometry by Analysis of Acoustic Pulse Response Measurements" Journal of Applied Physiology (1977) vol. 43, pp. 523-536.

Ware et al. "Continuous and Discrete Inverse-Scattering Problems in a Stratified Elastic Medium—I. Plane Waves at Normal Incidence" The Journal of Acoustical Society of America (1969) vol. 45, No. 4, pp. 911-921.

Faber et al. "Flextube Reflectometry for Localization of Upper Airway Narrowing—A Preliminary Study in Models and Awake Subjects" Respiratory Medicine (2001) vol. 95, pp. 631-638.

Carrive et al. "Biophony: An Open System to Measure the Airway Area by Acoustic Reflection" 18.sup.th Annual International Conference of the IEEE Engineering in Medicine and Biology Society (1996) pp. 125-126.

Murphy et al. "Spectral Characteristics of Lung Sounds in Patients with Chronic Obstructive Lung Disease" Faulkner Hospital, Boston, MA, presented at ATS 2004 (2002) one page.

Murphy et al. "Inhomogeneity of the Timing of Lung Sounds in Patients with Chronic Obstructive Lung Disease" Faulkner Hospital, Boston, MA, presented at ATS 2002 (2002) one page.

Murphy et al. "Lung Sound Patterns in Common Pulmonary Disorders" Faulker Hospital, Boston, MA, presented at ATS 2002 (2002) one page.

Huang et al. "Use of Intrinsic Modes in Biology: Examples of indicial response of pulmonary blood pressure to +− step hypoxia", Proc. Natl. Acad. Sci. USA vol. 95, pp. 12766-12771, Oct. 1998.

Huang et al. "Engineering analysis of biological variables: An example of blood pressure over 1 day", Proc. Natl. Acad. Sci. USA vol. 95, pp. 4816-4821, Apr. 1998.

Huang, Norden E. et al, The Empirical Mode Decomposition and the Hilbert Spectrum for Nonlinear and Non-Stationary Time Series Analysis, Proc. Roy Soc. London, pp. 903-955, .COPYRGT. 1998.

Huang, Norden E. et al, (Abstract)—A New View of Nonlinear Waves; The Hilbert Spectrum, Annual Review of Fluid Mechanics, Jan. 1999.

Katz Richard A., Chaotic Circuits for Communication, International Society for Optical Engineering, vol. 2612, Oct. 1995.

Ono, M. et al.; "Separation of Fine Crackles from Vesicular Sounds by a Nonlinear Digital Filter"; IEEE Transactions on Biomedical Engineering; vol. 36; No. 2; pp. 286-291; Feb. 1989; XP 000186148.

Jingping, X. et al; "Spectrum Analysis of Lung Sounds"; Images of the Twenty First Century; vol. part 5; No. conf. 11; pp. 1676-1677; Nov. 9, 1989.

Basano, L. et al; "A DSP Breath Sound Analyser"; Proceedings of the International Symposium on Circuits and Systems, ESPOO; vol. 3; No. conf. 21; pp. 2631-2634; Jun. 7, 1988.

Gavriely, N et al. "Airflow Effects on Amplitude and Spectral Content of Normal Breath Sounds" American Physiology Society (1996) Vo. 80(1) pp. 5-13.

(56) References Cited

OTHER PUBLICATIONS

Rasanen, H et al, "Detection of Pocine Oleic Acid-Induced Acute Lung Injury Using Pulmonary Acoustics" Journal of Applied Physiology (2002) vol. 93, pp. 51-57.

Rasanen, J., et al. "Response of Acoustic Transmission to Positive Airway Pressure Therapy in Experimental Lung Injury" Intensive Care Med (2005) vol. 31, pp. 1434-1441.

Carroll, P "Screening Spirometry: Dispelling Myths to Optimize Use" RT Magazine (2005) pp. 1-4.

Kraman, SS "Speed of Low Frequency Sound Through Lungs of Normal Men" Journal of Applied Physiology (1983) vol. 66 pp. 278-281.

Kraman, SS et al. "Transmission to the Chest of Sound Introduced at the Mouth" Journal of Applied Physiology (1989) vol. 66, pp. 278-281.

Berger, PJ et al. "Velocity and Attenuation of Sound in the Isolated Fetal Lung as it is Expanded with Air" Journal of Applied Physiology (2005) vol. 98, pp. 2235-2241.

Pedersen, PC et al., "Ultrasound Properties of Lung Tissue and Their Measurements" Ultrasound in Med. & Biol. (1986) vol. 12, No. 6, pp. 483-499.

Dunn, F "Attenuation and Speed of Ultrasound in Lung: Dependence Upon Frequency and Inflation" J. Acoust. Soc. Am. 80(4) (1986) pp. 1248-1250.

Pohmann, A et al. "Can Human Acoustic Respiratory Impedance Form the Basis for Lung Imaging?" Medical and Biological Engineering & Computing (1999) vol. 37, Supp. 2, Pt. II, pp. 952-0953.

Goncharoff, V., et al. "Wideband Acoustic Transmission of Human Lungs" Medical and Biological Engineering & Computing (1989) vol. 27, No. 5, pp. 513-519.

Piirila et al., "Objective Assessment of Cough," Eur Respir J, 1995, 8, 1949-1956.

Lukocius, et al., The Respiration Rate Estimation Method based on the Signal Maximums and Minimums Detection and the Signal Amplitude Evaluation, Electr. and Elect. Engr. 2008, No. 8(88).

COUGH DETECTOR

CROSS REFERENCE TO RELATED APPLICATION

This application is a continuation of U.S. patent application Ser. No. 11/912,897 with a 371 filing date of May 18, 2008, which issued as U.S. Pat. No. 8,241,223, on Aug. 14, 2012, which claims priority under 35 USC §371 to PCT/IL06/00517 having an international filing date of Apr. 30, 2006, which claims the benefit of U.S. Provisional Application 60/675,829, filed Apr. 29, 2005, which are incorporated herein by reference.

FIELD OF THE INVENTION

This invention relates to detection of signals from the body of a person or an animal and more specifically to the detection of cough.

BACKGROUND OF THE INVENTION

Physiology

Cough is a physiological reflex that helps clear secretions and foreign elements from the airways. The cough reflex is triggered by stimulation of mechano-receptors in the larynx, trachea, main carina and central airways. The afferent sensory signals are transmitted via pharyngeal branches of the glossopharyngeal nerve and by sensory fibers of the vagus nerve to the medulla oblongata. The signals are processed and a motor sequence of muscle activation is generated to create the cough.

Each cough starts with an inspiration, followed by closure of the glottis while the expiratory muscles (rectus abdominis and the intercostals muscles) contract. This contraction against a closed glottis rapidly elevates the intra-thoracic pressure. The glottis then opens and a burst of exhaled air flows through the trachea and out the mouth. The balance of forces on the tracheal wall, which includes the Bernoulli Effect, creates a net negative transmural pressure and dynamic tracheal collapse. As the trachea gets narrower, the speed of the air molecules through it increases, which further increases the negative transmural pressure and promotes additional collapse. The speed of air in the trachea during a cough may reach 100 m/s. The rapid gas movement along the tracheal walls creates substantial sheer forces, which help dislodge particles and secretions from the wall and into the air stream. These elements are them swept away with the gas outside of the airways through the glottis.

Each cough may have one or more components, or bursts for a single inspiration. Each burst is terminated by one of the following three mechanisms: (a) re-closure of the glottis, (b) termination of the expiratory muscles activity, or (c) exhaustion of the available gas flow reserve in the lung.

Patho-Physiology

While the cough reflex is an important component of the lung defense mechanisms, it is often a source of annoyance and concern to the patient. Chronic cough (i.e., frequent coughing that lasts for 2 weeks or more) may be an important sign of a lung disease (e.g., asthma, chronic bronchitis, malignancy, bronchiectasis, lung fibrosis or TB). There are, however, many cases where persistent cough is self-perpetuating, so that each cough spell applies such forces to the airway mucosa that stimulates and triggers a subsequent paroxysm, even in the absence of secretions or foreign bodies in the airways ("dry cough").

Epidemiology

The prevalence of cough is high, leading to more visits to Drs' offices than any other single clinical symptom or sign. It is estimated that as many as 3% of all office visits to primary care physicians in the US are due to cough. Consequently, the market for cough remedies is huge, extending from various natural herbs and aromatic syrups to narcotic habit-forming drugs (e.g. codeine). The total market of antitussive medications in the US alone is estimated in Billions of $US.

Cough Detection

With cough being such a common problem, the need for methods and devices for objective detection and quantification of cough is obvious. Cough detection is needed in order to assess the severity of cough in an individual patient, to determine the association between coughing and certain offending conditions, such as occupational exposure, and for the evaluation and validation of the effectiveness of new and old cough remedies.

There have been several methods for detection of cough and for the creation of a log of coughing activity in a person or an animal. The simplest and, to this time, the most accurate method of detecting cough is by one or more trained observers who are either present in person with the index patient, or are listening and observing a video tape recording of the patient. As such, this method is often used as a reference ("gold standard") for validation of an automated cough detection device.

Automated cough detection has been attempted and the following is a brief description of the available prior art. These methods may be divided into those that use the cough sound alone and those that use the cough sound in combination with other signals. Cough detection by loud-sound detection and recording on a sound-activated tape (or digital) recorder have been used in research by Mori et al. (1987) and Sestini at al. (1991). The timing of the tape activation may also be recorded with each loud sound. The total recording time, or the number of recorder activations are used as a cough activity index. This method is sensitive, but lacks specificity since other loud noises in the environment may trigger the recording as well. Subsequent auditory screening of the recorded sounds by a trained observer, or an automated algorithm (see below) may improve the specificity of this method.

Earis and co-workers (1994, 2002, 2003) described digital signal processing methods including spectral analysis and voice analysis methods to evaluate loud sounds to differentiate between cough sounds and other sounds such as vocalization. These studies as well as studies by other researchers analyzed ambient sounds recorded with a single microphone.

Other methods to detect coughs use two or more signals. Bush et al., described a method by which a microphone output is used in combination with the signals from Electromyograph (EMG) electrodes placed on the abdominal muscles. These muscles contract in order to generate the elevated expiratory intra-thoracic pressure needed for an effective cough. Salmi et al. (Chest, 1988) used a static charge-sensitive bed to detect the cough-induced fast movements of the body and an ambient microphone output. Gavriely N. described in U.S. Pat. Nos. 6,261,238 and 6,168,568 a method in which the loud output of a microphone alongside a simultaneous sudden motion of the chest detected by a chest motion detector such as an electrical impedance plethysmograph are used as the first phase of cough detection algorithm.

DETAILED DESCRIPTION OF THE PRESENT INVENTION

Figure 1:
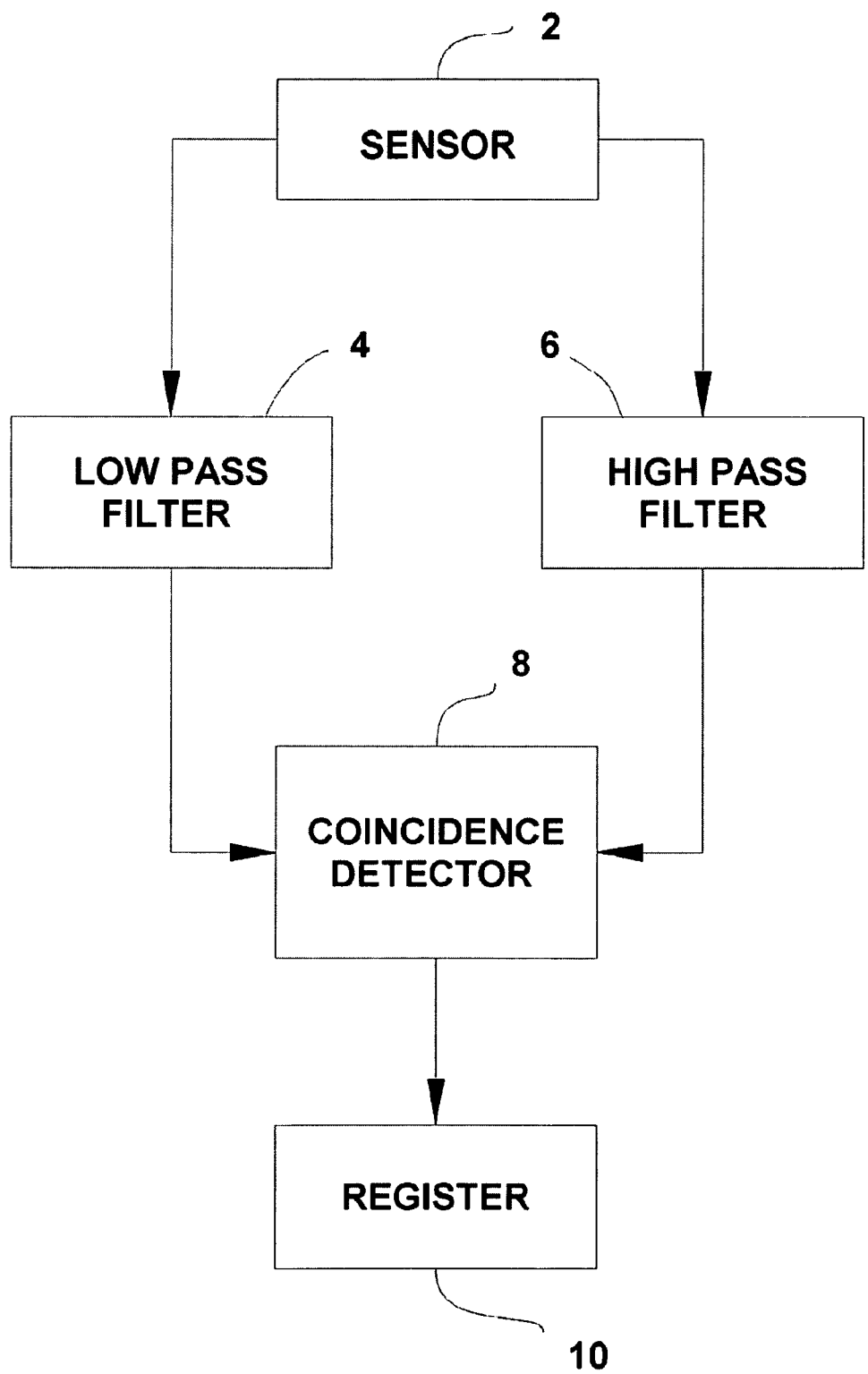
FIG. 1 is block diagram description of the structural aspects of a cough detector of the invention.
Figure 6A:
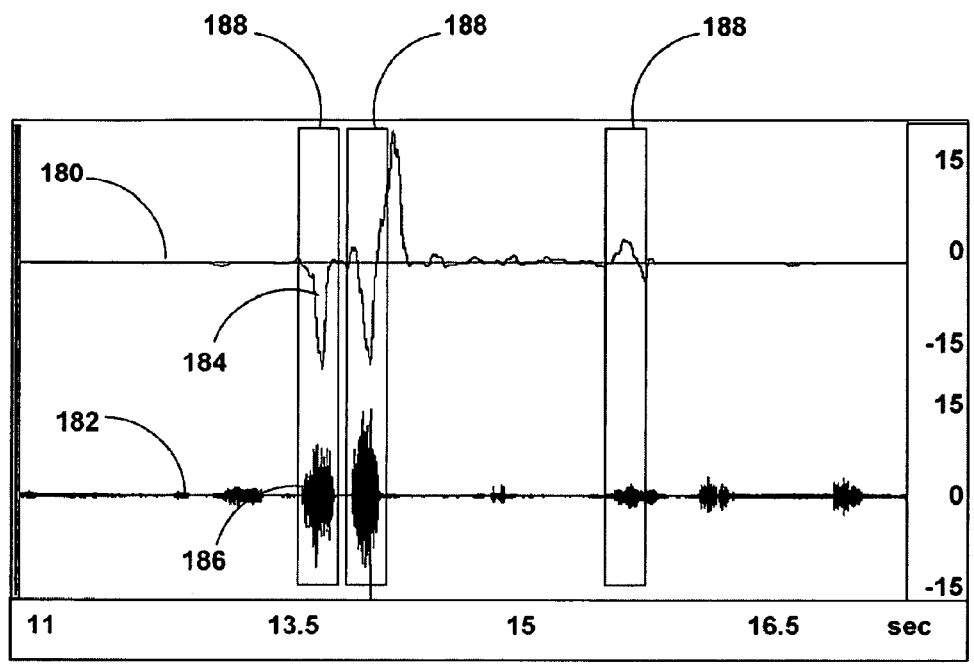
FIG. 6A is a graphic depiction of the low and high frequency components of the deformation cough detector sensor output during coughs.
Figure 6B:
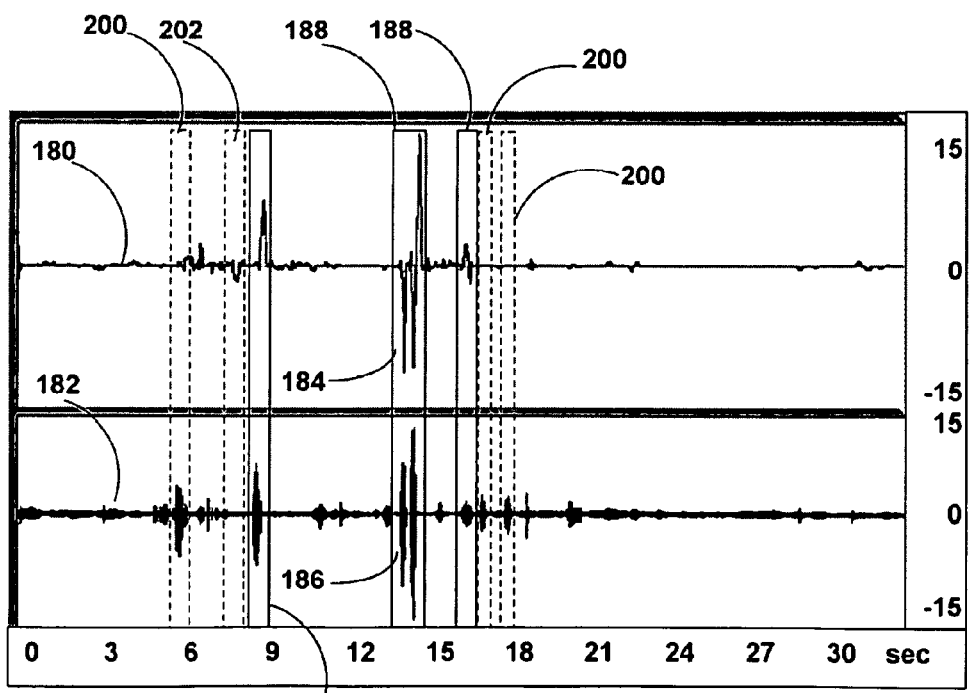
FIG. 6B is a graphic depiction of the low and high frequency components of the deformation cough detector during cough and during non cough activities.

In accordance with the present invention, a cough detector is provided that identifies coughs and draws a distinction between coughing sounds and other loud noises. It also differentiates between cough-induced rapid movement of tracheal air and other rapid movements. A sensor placed over the trachea at the anterior cervical area is used to collect the sound signals. The sensor collects the signal and transduces it into an electric signal. Any sensor known in the art able to detect simultaneously, both the high frequency acoustic signal of cough and the low frequency mechanical signal generated by the rapid flow of air and tracheal deformation during cough is applicable. The detection of the two frequencies may be achieved using a single sensing element in which case the sensor is simple, or alternatively by two separate sensing elements packaged together, in which case the sensor is compound. An example of a system embodying the invention is described schematically in FIG. 1 to which reference is now made. The electrical output of the sensor 2 is channeled to two separate frequency filters 4 and 6. Low pass filter 4 selectively passes signals associated with events that correspond to the rapid expiratory flow of air in the trachea or the sudden change in the tracheal dimensions associated with its dynamic collapse during cough. Such events typically generate vibrations in the frequency range of 0.5 to 10 Hz. High pass filter 6 selectively passes signal associated with brief loud sounds in the frequency range of 200 to 2000 Hz. The amplitude threshold is typically 70 dB absolute sound level pressure or higher and the duration threshold is typically between 0.15 to 1.5 sec or narrower. Coincidence detector 8 receives signals from both filters. In the event that signals from both filters arrive simultaneously, coincidence detector identifies the event as a coughing event. This data is then transmitted to a data register 10 that keeps log of the coughing activity detected by sensor 2. Examples of coughs where both thresholds are violated at the same time are shown in FIG. 6A and of acoustic and mechanical events that did and did not coincide are shown in FIG. 6B.

Figure 2A:
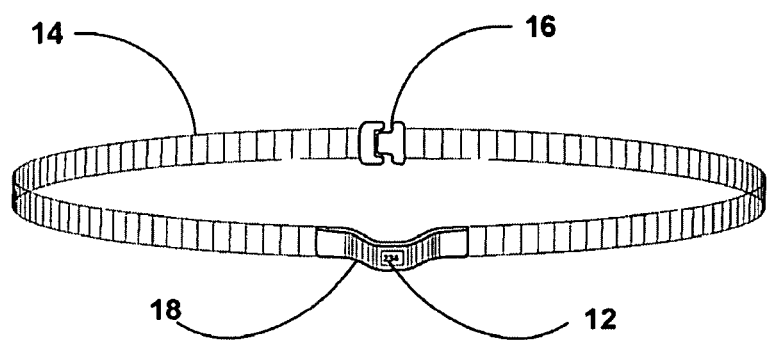
FIG. 2A is a schematic isometric description of the cough detector.
Figure 2B:
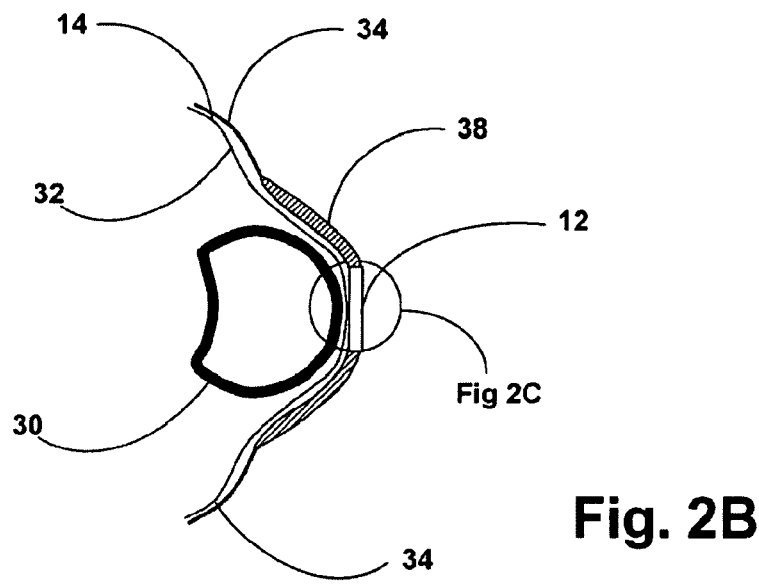
FIG. 2B is a transverse section through the frontal active element of the 5 deformation cough detector.

A cough detector in accordance with the present invention has a sensor that is donned on the neck and is self-enclosed with all the electronic elements necessary for the thresholds detection and data logging. In FIG. 2A to which reference is now made, a cough detector (CD) 12 hung by the circumferential band 14 around the neck so that the CD and positioned over the lower segment of the cervical trachea is shown. A latch 16 is used to adjust the length and the tension of the band 14 to fit snuggly to the neck yet without strangulating the patient. The active element 12 of the CD optionally includes a visible display of the cough activity 18, or a decorative element. In FIG. 2B to which reference is now made, an enlarged cross section of the trachea 30 is shown under the patient's skin 32.

Figure 2C:
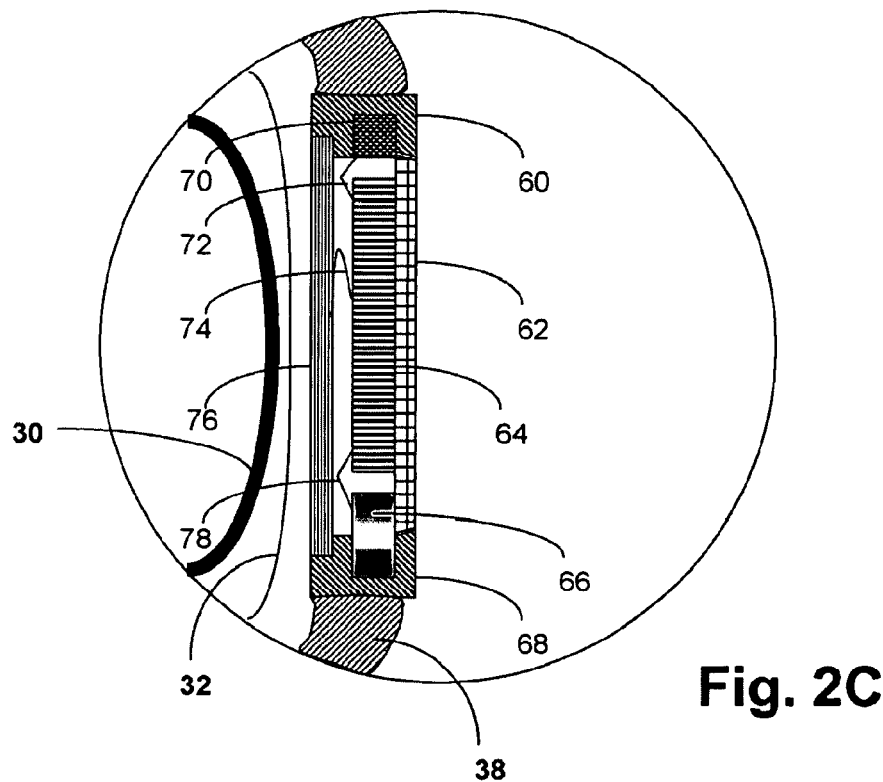
FIG. 2C is an enlarged transverse section through the active detection element of the deformation cough detector

The frontal ends of the circumferential band 34 are shown connected to the housing strap of the CD 38. The active element of the CD 12 is connected on both sides to the housing strap 38 and is in close contact with the pre-tracheal skin surface 32. The main components of the active element of the CD are shown in an enlarged form in FIG. 2C to which reference is now made. Sections of the tracheal wall 30 and the overlying skin 32 are also shown. The housing of the active element 60 is shown connected to the housing strap 38. The housing 60 holds within it an optional display 62 and a processor 64 that contains the electronic and/or digital technology needed to analyze, store, retrieve, display or transmit the data. The CD active element is powered by a battery 66 that is held in a groove 68 in the housing 60. The battery is connected to the processor 64 via wires 78. The stored data may be transmitted to a remote host computer or data logger (not shown) via a wire or wireless transmitter 70 connected to the processor 64 via wires 72. The sensing element 76 of the CD active element is capable of picking up both low and high frequency mechanical oscillations when brought into contact with the skin 32 overlaying the trachea 30. A preferred embodiment of the sensing element 76 is a piezoelectric crystal mounted on a metallic membrane such as model KBS-27DA-5AS transducer, commercially available from Kyocera Corporation of Japan. The sensor 76 is shown connected to the processor 64 via wires 74.

Figure 3:
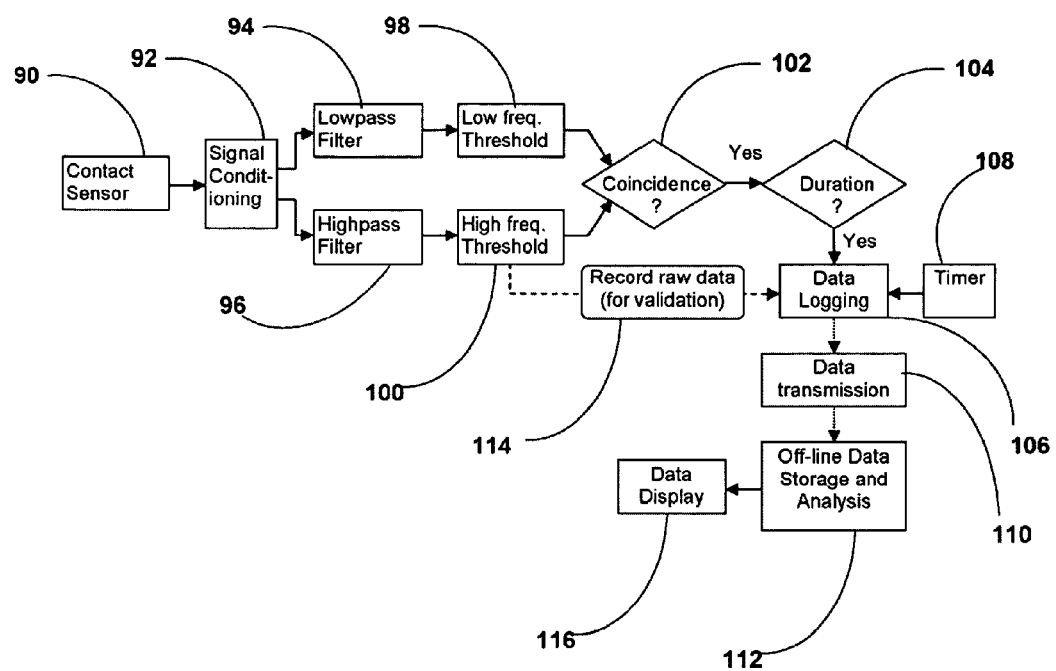
FIG. 3 is a block diagram of the detection method of the deformation cough detector.

A block diagram or a preferred embodiment of the deformation CD method is shown in FIG. 3 to which reference is now made. The signal from the contact sensor 90 is amplified in the signal conditioning element 92 and then filtered by the lowpass filter 94 and the highpass filter 96. The filtration of the signal is within low and high frequency ranges as outlined above. The low frequency signal is transmitted to a low frequency threshold detector 98 that identifies events where the low frequency signal is higher than the threshold. The threshold may be a fixed or adaptive threshold. For the duration that the low frequency threshold has been exceeded the low frequency threshold detector 98 emits a signal, which may be either analog, or digital. The high frequency signal is transmitted to a high frequency threshold detector 100 which identifies events that are of higher amplitude than the threshold. Here, too, the threshold may be fixed or adaptive. For the duration that the high frequency threshold has been exceeded the high frequency threshold detector 100 emits a signal, which may be either analog, or digital. Both signals are then transmitted to a coincidence detector 102 which determines whether the signals arriving from the low and the high frequency channels are simultaneous. If the signals are determined to be coincidental, the coincidence detector 102 generates a continuous signal for the duration of the coincidence. This signal is then transmitted to the duration detector 104, which determines whether the duration of the coincidental signal was within the range of cough durations as outlined above. If the duration of the coincidence was within the range, the duration detector 104 generates a signal that activates the data logging unit 106. The time of the event is also recorded on the data logger from a timing (clock) device 108. This event may also trigger recordation of a segment of raw data (sounds) from the time duration of 2-3 seconds that preceded the trigger event and were continuously tracked and transiently recorded by the recording element 114. This recording may be used for additional signal processing or for validation through listening by experts. The information from the data logger 106 may then be transmitted by means of a data transmission element 110 which may be via wire, or wireless and may be in a digital or an analog format. The data is transmitted to another data storage device for permanent recordation, further analysis 112, validation or for preparation for display by the data display member 116.

Figure 4:
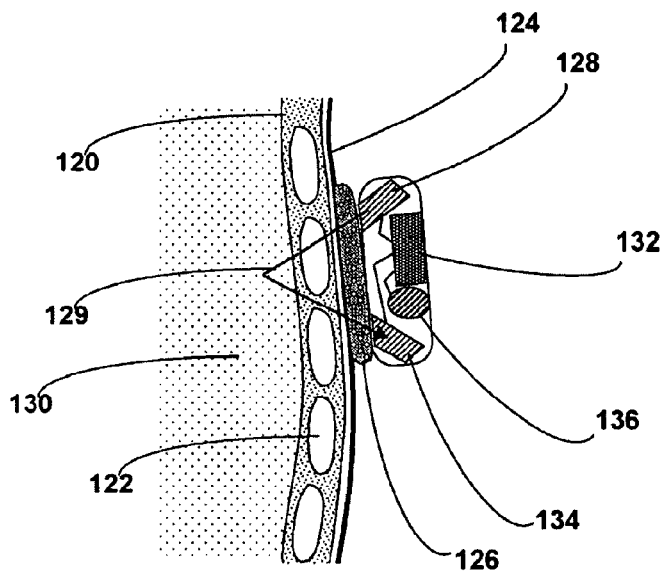
FIG. 4 is a longitudinal section through the ultrasonic cough detector.

An alternative preferred embodiment of the CD is based on detection of the acute sudden expiratory tracheal flow and deformation generated by coughing through an ultrasonic flow detector shown in FIG. 4 to which reference is now made. A longitudinal sagittal section through the tracheal wall 120 and its cartilage rings 122 and overlaying skin 124 is shown. The sensing element is coupled to the neck surface by an acoustically conductive jell pad 126, which facilitates the transmission of the ultrasonic signal generated by emitter 128. The ultrasonic signal, represented by the arrow 129 is reflected by the air flow and the minute particles that carried along 130 to reach the ultrasonic receiver 134. The moving air and suspended particles change in the received sound relative to the emitted sound in the form of a Doppler frequency shift that is detected by the processor 132 powered by the battery 136. The processor 132 also generates the oscillations needed to create the ultrasonic signal and may also contain an integrated microphone for detection of the cough sounds.

Figure 5:
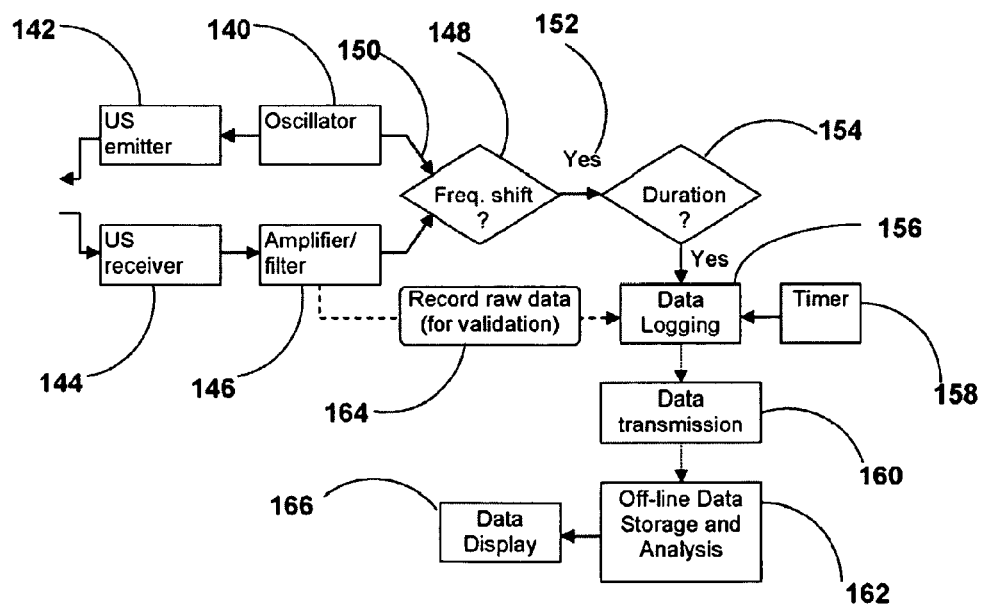
FIG. 5 is a block diagram of the detection method of the ultrasonic cough detector.

The operation of the ultrasonic CD is described in the block diagram shown in FIG. 5 to which reference is now made. Oscillator 140 generates an ultrasound frequency energy that drives the ultrasonic emitter 142. The returning signal is picked up by the ultrasonic receiver 144 and amplified by the amplifier 146. The frequency shift detector 148 receives the signals from the amplifier 146 and through a secondary channel 150 the signal from the oscillator 140. The frequency shift detector 148 determines if there was a frequency shift and if this frequency shift exceeded a threshold. If the threshold was exceeded as indicated by the yes over the arrow 152, a signal is transmitted from the frequency shift detector 148 to the duration detector 154. In an alternative embodiment, the coincidence between the signal indicating that the frequency shift threshold was exceeded and the high frequency signal from the microphone built into the sensor (not shown) is evaluated. Only if there is a coincidence between the timing of both signals the duration detector 154 receives a signal. The duration detector 154 determines if the duration of the signal it receives is within the time duration of a cough as described above and if so, generates a signal that triggers the data logging element 156 to register the event as the presence of a cough. In addition, the time of the event, determined by the timer 158 is recorded in the data logger. Optionally, the raw data from the preceding time period of 2-3 seconds, transiently stored in the raw data recorder 164 may be recorded in the data logger 156 for subsequent analysis or validation. The data stored in the data logger 156 may be transmitted via a transmission element 160 to a permanent storage and analysis element 162 via wire or wireless transmission as a digital or an analog signal. The data from the analyzer 162 may be displayed in graphic or numeric form by the data display element 166.

Data from actual coughs from a patient are shown in FIG. 6A to which reference is now made. The top tracing 180 and the bottom tracing 182 are both plots of amplitude vs. time. The top tracing 180 is the low frequency component of the piezoelectric signal and the bottom tracing 182 is the high frequency component of the piezoelectric signal. The deflection 184 of the low frequency tracing 180 and the oscillation 186 of the high frequency component tracing 182 coincide as indicated by the rectangle 188 that surround both of them. Likewise, the two other rectangles 188 surround events where the low frequency motion of the trachea and the high frequency sound of the trachea coincide, indicating the presence of a cough. The duration of each event is within the time duration of a cough, which confirms that these events are actually coughs.

A wider time frame, which includes the same recording that is shown in FIG. 6A, is shown in FIG. 6B to which reference is now made. The low frequency component 180 and the high frequency component of the piezoelectric sensor are shown. Events in which substantial low frequency tracheal motion 184 coincides with the high frequency loud sounds 186 and represent coughs are shown surrounded by solid rectangles 188. In contrast, events in which there was only high frequency sound are surrounded by broken line rectangles 200 while an event in which only low frequency activity was present is surrounded by a broken line 202. This figure demonstrates the discrimination ability of this new method to differentiate between genuine cough, generated by the index subject and cough-like noises or body motion that are not due to the index subject cough.

Another preferred embodiment of the CD is based on detection of the acute sudden expiratory tracheal flow and deformation generated by coughing through detection of a sudden change in the electrical resistance of the neck. A plurality of electrodes are attached to the neck and transmit an alternating minute current in the range of 5-50 kHz. At least two electrodes are placed adjacent to the sides of the trachea with additional optional electrode used as reference and placed elsewhere around the circumference of the neck. The voltage to current relationship, usually defined as the electrical impedance is continuously tracked. When the person coughs, a sudden change in the tracheal dimensions causes an abrupt transient change in the electrical impedance. This is a direct measure of the motion, which when combined with the sound detected by a microphone or a contact sensor is used to positively identify coughs in the same scheme outlined for the previous two examples described above.

It is clear that any combination of low and high frequency signals may be used.

What is claimed:

1. A cough detector adapted to externally engage a person comprising:
    a sensor capable of sensing and transducing low frequency and high frequency mechanical vibrations;
    a low pass filter for receiving signals from the sensor wherein the low pass filter is adapted to selectively pass low frequency signals within a frequency range of 0.5 Hz to 10 Hz;
    a low frequency threshold detector for applying an adaptive or fixed threshold to the low frequency signals;
    a high pass filter for receiving signals from the sensor wherein the high pass filter is adapted to selectively pass high frequency signals within a frequency range of 200 Hz to 2000 Hz;
    a high frequency threshold detector for applying an adaptive or fixed threshold to the high frequency signals;
    a coincidence detector for receiving signals from both the low frequency threshold detector and the high frequency threshold detector, wherein the coincidence detector identifies a coincidence between the signals arriving from the low frequency threshold detector and the high frequency threshold detector and generates a continuous signal for the duration of the coincidence;
    a duration detector for determining whether the duration of the continuous signal generated by the coincidence detector is within a range of cough durations, to thereby identify coughing events; and a register for storing data concerning coughing events identified as such by the duration detector.

2. The device of claim 1, wherein the data concerning the coughing events is transmitted to a remote host computer or data logger via a wire or wireless transmitter.

3. The device of claim 1, wherein the range of cough durations is between 0.1 to 1.5 seconds.

4. A method for detecting and counting coughing events, the method including:

a) positioning a cough detector on the lower segment of the cervical trachea of a patient wherein the cough detector comprises:

a sensor capable of sensing and transducing mechanical vibrations, a low pass filter for receiving signals from the sensor wherein the low pass filter is adapted to selectively pass low frequency signals within a frequency range of 0.5 Hz to 10 Hz, a low frequency threshold detector for applying an adaptive or fixed threshold to the low frequency signals, a high pass filter for receiving signals from the sensor wherein the high pass filter is adapted to selectively pass high frequency signals within a frequency range of 200 Hz to 2000 Hz, a high frequency threshold detector for applying an adaptive or fixed threshold to the high frequency signals, a coincidence detector for receiving signals from both the low frequency threshold detector and the high frequency threshold detector, wherein the coincidence detector identifies a coincidence between the signals arriving from the low frequency threshold detector and the high frequency threshold detector and generates a continuous signal for the duration of the coincidence, a duration detector for determining whether the duration of the continuous signal generated by the coincidence detector is within a range of cough durations, to thereby identify coughing events, and a register for storing data concerning coughing events identified as such by the duration detector;

b) filtering a signal from the sensor with a low pass filter therein selectively passing low frequency portion of the signal within a frequency range of 0.5 Hz to 10 Hz and filtering the signal with a high pass filter therein selectively passing high frequency portion of the signal within a frequency range of 200 Hz to 2000 Hz;

c) applying a fixed or adaptive low pass threshold to the low pass filtered signal with a low frequency threshold detector;

d) applying a fixed or adaptive high pass threshold to the high pass filtered signal with a high frequency threshold detector;

e) identifying a coincidence between a high frequency signal from the high frequency threshold detector and a low frequency signal from the low frequency threshold detector; and f) determining, by a duration detector, whether the duration of the coincidence is within the range of cough durations to thereby identify coughing events.

5. The method of claim 4, wherein the threshold is a duration based threshold.

6. The method of claim 5, wherein the duration threshold is below 1.5 seconds.

7. The method of claim 4, wherein the coughing event triggers communication with a processor or computer.

8. A system adapted to externally engage a person and assess coughing comprising:

a sensor capable of sensing and transducing low frequency and high frequency mechanical vibrations;

a low pass filter for receiving signals from the sensor wherein the low pass filter is adapted to selectively pass low frequency signals within a frequency range of 0.5 Hz to 10 Hz;

a low frequency threshold detector for applying an adaptive or fixed threshold to the low frequency signals;

a high pass filter for receiving signals from the sensor wherein the high pass filter is adapted to selectively pass high frequency signals within a frequency range of 200 Hz to 2000 Hz;

a high frequency threshold detector for applying an adaptive or fixed threshold to the high frequency signals;

a coincidence detector for receiving signals from both the low frequency threshold detector and the high frequency threshold detector, wherein the coincidence detector identifies a coincidence between the signals arriving from the low frequency threshold detector and the high frequency threshold detector and generates a continuous signal for the duration of the coincidence;

a duration detector for determining whether the duration of the continuous signal generated by the coincidence detector is within a range of cough durations, to thereby identify coughing events; and a register for storing data concerning coughing events identified as such by the duration detector.

9. The system of claim 8, further comprising a data logging element wherein the duration detector generates a signal that triggers the data logging element to register the presence of a cough.

10. The system of claim 8, wherein the register logs the presence of a cough.

11. The system of claim 8, wherein the data concerning coughing events is displayed.

* * * * *